(12) United States Patent
Tung et al.

(10) Patent No.: US 7,837,939 B2
(45) Date of Patent: Nov. 23, 2010

(54) RAPID SAMPLE COLLECTION AND ANALYSIS DEVICE AND METHODS OF USE

(75) Inventors: Hsiaoho E. Tung, San Diego, CA (US); Yuzhang Wu, Hangzhou (CN); Jeilin Dai, Hangzhou (CN); Ying Yang, Hangzhou (CN)

(73) Assignee: Alere Switzerland GmbH, Zug (CH)

( * ) Notice: Subject to any disclaimer, the term of this patent is extended or adjusted under 35 U.S.C. 154(b) by 435 days.

(21) Appl. No.: 11/894,108

(22) Filed: Aug. 20, 2007
(Under 37 CFR 1.47)

(65) Prior Publication Data

US 2009/0117665 A1 May 7, 2009

Related U.S. Application Data (63) Continuation of application No. 11/433,053, filed on May 12, 2006, now abandoned, which is a continuation of application No. PCT/US2004/038427, filed on Nov. 15, 2004.

(60) Provisional application No. 60/520,437, filed on Nov. 14, 2003.

(51) Int. Cl.
*G01N 21/00* (2006.01)
*G01N 31/22* (2006.01)

(52) U.S. Cl. .............................. 422/58; 422/50; 422/55; 422/61; 422/68.1; 436/518; 436/164; 436/165; 435/283.1; 435/287.1; 435/288.7

(58) Field of Classification Search ................... 422/58, 422/50, 55, 61, 68.1; 436/518, 164, 165; 435/283.1, 287.1, 288.7

See application file for complete search history.

(56) References Cited

U.S. PATENT DOCUMENTS 3,896,974 A 7/1975 McIntosh (Continued)

FOREIGN PATENT DOCUMENTS

CN 1084045 A 3/1994

(Continued)

OTHER PUBLICATIONS

U.S. Appl. No. 60/233,739, filed Sep. 19, 2000, Tung et al.

(Continued)

*Primary Examiner*—Melanie Yu
(74) *Attorney, Agent, or Firm*—DLA Piper LLP (US)

(57) ABSTRACT

The present invention is directed to devices and methods for determining the presence of analyte in a fluid sample. The devices utilize a sample collection well, an expression plate for expressing sample into the sample collection well, a plunger that drives a lance, and a test compartment containing test elements. The devices also preserve an aliquot of fluid sample in a reservoir for later confirmation testing. When the plunger is lowered into the sample collection well, a lance on the device punctures a frangible material that covers a sample outlet. When the sample outlet is thus opened, fluid sample flows from the sample collection cup to the test compartment. In one embodiment the plunger is lowered as a cap is applied to the device. The devices are useful for detecting the presence of analyte in a wide variety of fluid samples, such as saliva, oral fluids, and more. The invention also provides methods of using the devices, and kits containing the devices.

23 Claims, 6 Drawing Sheets

U.S. PATENT DOCUMENTS

| | | | |
|---|---|---|---|
| 4,014,748 A * | 3/1977 | Spinner et al. | 600/572 |
| 4,114,605 A | 9/1978 | McGhee et al. | |
| 4,275,149 A | 6/1981 | Litman et al. | |
| 4,299,916 A | 11/1981 | Litman et al. | |
| 4,458,020 A | 7/1984 | Bohn et al. | |
| 4,635,488 A | 1/1987 | Kremer | |
| 4,768,238 A | 9/1988 | Kleinberg et al. | |
| 4,771,486 A | 9/1988 | Gutierrez et al. | |
| 4,817,632 A | 4/1989 | Schramm | |
| 4,853,325 A | 8/1989 | Vodian et al. | |
| 4,857,453 A | 8/1989 | Ullman et al. | |
| 4,877,850 A | 10/1989 | Geibel et al. | |
| 4,886,175 A | 12/1989 | Schlaudecker | |
| 4,923,798 A | 5/1990 | LeMoine et al. | |
| 4,955,745 A | 9/1990 | Vauquelin | |
| 4,962,025 A * | 10/1990 | Moldowan | 435/25 |
| 5,050,616 A | 9/1991 | Wolff et al. | |
| 5,073,484 A | 12/1991 | Swanson et al. | |
| 5,076,474 A | 12/1991 | Hansen | |
| 5,119,831 A | 6/1992 | Robin et al. | |
| 5,160,329 A * | 11/1992 | Oxley | 604/317 |
| 5,170,799 A | 12/1992 | Nagase et al. | |
| 5,185,127 A | 2/1993 | Vonk | |
| 5,186,900 A * | 2/1993 | Jensen et al. | 422/104 |
| 5,211,182 A | 5/1993 | Deutsch et al. | |
| 5,234,001 A | 8/1993 | Goldstein et al. | |
| 5,246,145 A | 9/1993 | Leoncavallo et al. | |
| 5,252,496 A | 10/1993 | Kang et al. | |
| 5,260,031 A | 11/1993 | Seymour | |
| 5,261,572 A | 11/1993 | Strater | |
| 5,275,785 A | 1/1994 | May et al. | |
| 5,328,058 A | 7/1994 | Leoncavallo et al. | |
| 5,334,502 A | 8/1994 | Sangha | |
| 5,339,829 A | 8/1994 | Thieme et al. | |
| 5,352,410 A | 10/1994 | Hansen et al. | |
| 5,376,337 A | 12/1994 | Seymour | |
| 5,380,492 A | 1/1995 | Seymour | |
| 5,393,496 A | 2/1995 | Seymour | |
| 5,415,994 A | 5/1995 | Imrich et al. | |
| 5,416,000 A | 5/1995 | Allen et al. | |
| 5,424,193 A | 6/1995 | Pronovost et al. | |
| 5,479,937 A | 1/1996 | Thieme et al. | |
| 5,494,646 A | 2/1996 | Seymour | |
| 5,504,013 A | 4/1996 | Senior | |
| 5,559,041 A | 9/1996 | Kang et al. | |
| 5,573,009 A | 11/1996 | Thieme et al. | |
| 5,573,099 A | 11/1996 | Church et al. | |
| 5,602,040 A | 2/1997 | May et al. | |
| 5,609,160 A | 3/1997 | Bahl et al. | |
| 5,622,871 A | 4/1997 | May et al. | |
| 5,654,162 A | 8/1997 | Guire et al. | |
| 5,656,503 A | 8/1997 | May et al. | |
| 5,679,535 A | 10/1997 | Joyce et al. | |
| 5,686,315 A | 11/1997 | Pronovost et al. | |
| 5,712,170 A | 1/1998 | Kouvonen et al. | |
| 5,714,341 A | 2/1998 | Thieme et al. | |
| 5,736,322 A | 4/1998 | Goldstein | |
| 5,738,634 A | 4/1998 | Caillouette | |
| 5,766,961 A | 6/1998 | Pawlak et al. | |
| 5,770,460 A | 6/1998 | Pawlak et al. | |
| 5,786,227 A | 7/1998 | Charlton | |
| 5,786,228 A | 7/1998 | Charlton | |
| 5,786,427 A | 7/1998 | Kijima et al. | |
| 5,830,154 A | 11/1998 | Goldstein et al. | |
| 5,830,410 A | 11/1998 | Thieme et al. | |
| 5,910,122 A | 6/1999 | D'Angelo | |
| 5,916,815 A | 6/1999 | Lappe | |
| 5,922,283 A | 7/1999 | Hsu | |
| 5,935,864 A | 8/1999 | Schramm | |
| 5,965,453 A | 10/1999 | Skiffington et al. | |
| 5,965,458 A | 10/1999 | Kouvonen et al. | |
| 5,968,746 A | 10/1999 | Schneider | |
| 5,976,895 A | 11/1999 | Cipkowski | |
| 5,981,293 A | 11/1999 | Charlton | |
| 5,981,300 A | 11/1999 | Moll et al. | |
| 5,986,895 A | 11/1999 | Stewart et al. | |
| 6,022,326 A | 2/2000 | Tatum et al. | |
| 6,046,058 A | 4/2000 | Sun et al. | |
| 6,102,872 A | 8/2000 | Doneen et al. | |
| 6,136,610 A | 10/2000 | Polito et al. | |
| 6,140,136 A | 10/2000 | Lee | |
| 6,150,178 A * | 11/2000 | Cesarczyk et al. | 436/165 |
| 6,180,395 B1 * | 1/2001 | Skiffington et al. | 435/287.6 |
| 6,183,972 B1 | 2/2001 | Kuo et al. | |
| 6,187,268 B1 | 2/2001 | Albarella et al. | |
| 6,187,269 B1 | 2/2001 | Lancesseur et al. | |
| 6,187,598 B1 | 2/2001 | May et al. | |
| 6,194,221 B1 | 2/2001 | Rehg et al. | |
| 6,194,224 B1 | 2/2001 | Good et al. | |
| 6,221,678 B1 | 4/2001 | Chandler | |
| 6,223,947 B1 | 5/2001 | Bernard | |
| 6,228,660 B1 | 5/2001 | May et al. | |
| 6,235,241 B1 | 5/2001 | Catt et al. | |
| 6,241,689 B1 | 6/2001 | Chard et al. | |
| 6,248,598 B1 | 6/2001 | Bogema | |
| 6,271,046 B1 | 8/2001 | Chandler | |
| 6,277,587 B1 | 8/2001 | Lamster | |
| 6,277,646 B1 | 8/2001 | Guirguis et al. | |
| 6,291,178 B1 | 9/2001 | Schneider | |
| 6,297,020 B1 | 10/2001 | Brock | |
| 6,303,081 B1 | 10/2001 | Mink et al. | |
| 6,306,642 B1 | 10/2001 | Nelson et al. | |
| 6,316,205 B1 | 11/2001 | Guan et al. | |
| 6,338,969 B1 | 1/2002 | Shareef et al. | |
| 6,352,862 B1 | 3/2002 | Davis et al. | |
| 6,368,873 B1 | 4/2002 | Chang et al. | |
| 6,372,513 B1 | 4/2002 | Nguyen et al. | |
| 6,372,514 B1 | 4/2002 | Lee | |
| 6,372,515 B1 | 4/2002 | Casterlin et al. | |
| 6,372,516 B1 | 4/2002 | Sun | |
| 6,375,896 B1 | 4/2002 | Wuske et al. | |
| 6,375,897 B1 | 4/2002 | Bachand | |
| 6,379,620 B1 | 4/2002 | Tydings et al. | |
| 6,391,652 B2 | 5/2002 | Okada et al. | |
| 6,403,383 B1 | 6/2002 | Casterlin et al. | |
| 6,418,606 B1 | 7/2002 | Bachand | |
| 6,423,550 B1 | 7/2002 | Jenkins et al. | |
| 6,429,026 B1 | 8/2002 | Pettersson et al. | |
| 6,440,087 B1 | 8/2002 | Sangha | |
| 6,443,892 B1 | 9/2002 | Kidwell | |
| 6,464,939 B1 | 10/2002 | Bachand et al. | |
| 6,468,474 B2 | 10/2002 | Bachand et al. | |
| 6,485,982 B1 | 11/2002 | Charlton | |
| 6,489,172 B1 * | 12/2002 | Bachand et al. | 436/180 |
| 6,506,612 B2 | 1/2003 | Kang et al. | |
| 6,514,768 B1 | 2/2003 | Guire et al. | |
| 6,514,769 B2 | 2/2003 | Lee et al. | |
| 6,528,323 B1 | 3/2003 | Thayer et al. | |
| 6,537,823 B1 | 3/2003 | Smith | |
| 6,548,019 B1 | 4/2003 | Lee et al. | |
| 6,565,808 B2 | 5/2003 | Hudak et al. | |
| 6,656,744 B2 | 12/2003 | Pronovost et al. | |
| 6,669,908 B2 | 12/2003 | Weyker et al. | |
| 6,673,630 B2 | 1/2004 | Albarella et al. | |
| 6,730,268 B2 | 5/2004 | Lee et al. | |
| 6,780,160 B2 | 8/2004 | Zhou et al. | |
| 6,887,681 B2 | 5/2005 | DiCesare et al. | |
| 6,979,576 B1 | 12/2005 | Cheng et al. | |
| 7,048,693 B2 | 5/2006 | Zhou et al. | |
| 7,114,403 B2 | 10/2006 | Wu et al. | |
| 7,270,959 B2 | 9/2007 | Hudak | |
| 7,300,633 B2 | 11/2007 | Hudak et al. | |
| 7,481,977 B2 | 1/2009 | Percival et al. | |
| 7,517,495 B2 | 4/2009 | Wu et al. | |

| | | | | | | |
|---|---|---|---|---|---|---|
| 2001/0004532 A1 | 6/2001 | Chandler | EP | 0 734 685 A1 | 10/1996 |
| 2001/0008614 A1 | 7/2001 | Aronowitz | EP | 0 734 686 A1 | 10/1996 |
| 2001/0008774 A1 | 7/2001 | May et al. | EP | 0 753 148 B1 | 12/1998 |
| 2001/0021536 A1 | 9/2001 | Lee | EP | 1 216 931 A1 | 6/2002 |
| 2001/0023076 A1 | 9/2001 | Guan et al. | EP | 1 275 962 A1 | 1/2003 |
| 2001/0023324 A1 | 9/2001 | Pronovost et al. | EP | 1 348960 A1 | 10/2003 |
| 2001/0041368 A1 | 11/2001 | May et al. | GB | 855916 | 12/1960 |
| 2002/0001845 A1 | 1/2002 | Klaerner et al. | JP | 11-304800 A | 11/1999 |
| 2002/0004019 A1 | 1/2002 | Bachand et al. | WO | WO 92/16842 A1 | 10/1992 |
| 2002/0015663 A1 | 2/2002 | Goldstein et al. | WO | WO 93/11434 A1 | 6/1993 |
| 2002/0020713 A1 | 2/2002 | Kis et al. | WO | WO 94/07419 A1 | 4/1994 |
| 2002/0031840 A1 | 3/2002 | Albarella et al. | WO | WO 94/18892 A1 | 9/1994 |
| 2002/0031845 A1 | 3/2002 | Cipkowski | WO | WO 95/02822 A1 | 1/1995 |
| 2002/0052050 A1 | 5/2002 | Douglas et al. | WO | WO 95/07223 A2 | 3/1995 |
| 2002/0085953 A1 | 7/2002 | Parker | WO | WO 95/07223 A3 | 5/1995 |
| 2002/0085958 A1* | 7/2002 | Nemcek et al. ............ 422/102 | WO | WO 95/27205 A1 | 10/1995 |
| 2002/0098512 A1 | 7/2002 | Goodell et al. | WO | WO 97/20502 A1 | 6/1997 |
| 2002/0132267 A1 | 9/2002 | Wong | WO | WO 98/44158 A1 | 10/1998 |
| 2002/0132370 A1 | 9/2002 | Lassen et al. | WO | WO 99/06827 A2 | 2/1999 |
| 2002/0137231 A1 | 9/2002 | Cipkowski et al. | WO | WO 99/06827 A3 | 4/1999 |
| 2002/0146346 A1 | 10/2002 | Konecke | WO | WO 99/22639 A1 | 5/1999 |
| 2002/0150884 A1 | 10/2002 | Zmuda et al. | WO | WO 99/22645 A1 | 5/1999 |
| 2002/0155028 A1 | 10/2002 | Wong | WO | WO 99/27139 A1 | 6/1999 |
| 2002/0155029 A1 | 10/2002 | Mink et al. | WO | WO 99/50656 A1 | 10/1999 |
| 2002/0173047 A1 | 11/2002 | Hudak et al. | WO | WO 00/15020 A1 | 3/2000 |
| 2002/0192839 A1 | 12/2002 | Mink et al. | WO | WO 00/20862 A1 | 4/2000 |
| 2003/0045003 A1 | 3/2003 | Smith | WO | WO 00/25666 A1 | 5/2000 |
| 2003/0064526 A1* | 4/2003 | Niedbala et al. ............ 436/165 | WO | WO 00/64334 A1 | 11/2000 |
| 2003/0129088 A1 | 7/2003 | Lee et al. | WO | WO 01/08993 A1 | 2/2001 |
| 2003/0129673 A1 | 7/2003 | Schwarz et al. | WO | WO 01/81915 A1 | 11/2001 |
| 2003/0138971 A1 | 7/2003 | D'Aurora | WO | WO 01/49820 A1 | 12/2001 |
| 2003/0175992 A1 | 9/2003 | Toranto et al. | WO | WO 02/04941 A2 | 1/2002 |
| 2003/0175993 A1 | 9/2003 | Toranto et al. | WO | WO 02/07645 A2 | 1/2002 |
| 2003/0190259 A1 | 10/2003 | Alley | WO | WO 02/04942 A1 | 2/2002 |
| 2003/0207466 A1 | 11/2003 | Po Lee | WO | WO 02/16946 A2 | 2/2002 |
| 2004/0018636 A1 | 1/2004 | Zhou et al. | WO | WO 02/016946 A3 | 2/2002 |
| 2004/0082878 A1 | 4/2004 | Baldwin et al. | WO | WO 02/04941 A3 | 4/2002 |
| 2004/0184954 A1 | 9/2004 | Guo et al. | WO | WO 02/07645 A3 | 5/2002 |
| 2004/0191760 A1 | 9/2004 | Zhou et al. | WO | WO 02/058600 A2 | 8/2002 |
| 2005/0119589 A1 | 6/2005 | Tung et al. | WO | WO 02/058600 A3 | 8/2002 |
| 2005/0180882 A1 | 8/2005 | Tung et al. | WO | WO 02/059600 A2 | 8/2002 |
| 2005/0202568 A1 | 9/2005 | Tung et al. | WO | WO 02/059600 A3 | 8/2002 |
| 2006/0034728 A1 | 2/2006 | Kloepfer et al. | WO | WO 02/082040 A2 | 10/2002 |
| 2006/0121548 A1 | 6/2006 | Robbins et al. | WO | WO 02/082040 A3 | 10/2002 |
| 2006/0292035 A1 | 12/2006 | Gould et al. | WO | WO 02/096480 A2 | 12/2002 |
| 2007/0128070 A1 | 6/2007 | Wu et al. | WO | WO 02/096480 A3 | 12/2002 |
| 2009/0226883 A1 | 9/2009 | Wu et al. | WO | WO 2005/008216 A2 | 1/2005 |
| 2009/0232702 A1 | 9/2009 | Wu et al. | WO | WO 2005/050165 A2 | 6/2005 |
| | | | WO | WO 2005/008216 A3 | 7/2005 |
| FOREIGN PATENT DOCUMENTS | | | WO | WO 2005/050165 A3 | 7/2005 |
| | | | WO | WO 2007/062575 A1 | 6/2007 |
| CN | 1314593 A | 9/2001 | WO | WO 2008/012566 A2 | 1/2008 |
| CN | 2476023 Y | 2/2002 | WO | WO 2008/012566 A3 | 11/2008 |
| CN | 1603823 A | 4/2005 | | | |
| CN | 1614383 A | 5/2005 | | | |
| CN | 1645146 A | 7/2005 | | | |
| EP | 0 390 984 A1 | 10/1990 | | | |
| EP | 0 392 096 A1 | 10/1990 | | | |
| EP | 0 455 916 A2 | 11/1991 | | | |
| EP | 0 455 916 A3 | 11/1991 | | | |
| EP | 0 500 172 A1 | 8/1992 | | | |
| EP | 0 542 107 A1 | 5/1993 | | | |
| EP | 0 561 322 A1 | 9/1993 | | | |
| EP | 0 455 916 B1 | 2/1996 | | | |
| EP | 0 734 684 A1 | 10/1996 | | | |

OTHER PUBLICATIONS

International search report dated Jul. 19, 2006 for PCT Application No. US2004/038427.

International search report dated Feb. 1, 2007 for PCT Application No. CN2006/003028.

International search report dated Nov. 1, 2007 for PCT Application No. CN2007/70344.

International search report dated Mar. 16, 2009 for PCT Application No. IB2008/001831.

* cited by examiner

Top View

Section View A - A

RAPID SAMPLE COLLECTION AND ANALYSIS DEVICE AND METHODS OF USE

CROSS-REFERENCE TO RELATED APPLICATIONS

This application claims priority to PCT/US2004/038427, filed on Nov. 15, 2004; which claims priority to U.S. Provisional Application No. 60/520,437, filed Nov. 14, 2003, the contents of which are specifically incorporated herein.

FIELD OF THE INVENTION

The present invention is directed to devices for the rapid analysis of fluids for analytes of interest and the storage of those fluids.

BACKGROUND OF THE INVENTION

The following Background of the Invention is intended to aid the reader in understanding the invention and is not admitted to be prior art.

Illicit drug use is an established and growing problem in our society. In 2003, the US Department of Health and Human Services found that an estimated 19.5 million Americans or 8.2 percent of the population aged 12 or older, were current illicit drug users. Current illicit drug use means use of an illicit drug during the month prior to the US Department of Health and Human Services survey interview. Marijuana was found to be the most commonly used illicit drug, with a rate of 6.2 percent (14.6 million). An estimated 2.3 million persons (1.0 percent) were current cocaine users, 604,000 of whom used crack. Hallucinogens were used by 1.0 million persons, and there were an estimated 119,000 current heroin users.

To combat and monitor this problem, drug testing has become standard procedure in a variety of settings, such as employment, school, sports, law enforcement, and the like. To facilitate this effort, a drug-testing industry has emerged. This industry provides a variety of drug testing products. A typical product is a urine collection cup incorporating analysis tests. These devices can be complicated and difficult or messy to use, or they may pose special problems of sample adulteration by the subject trying to hide their recent drug abuse.

There is therefore a need for better methods and apparatuses for performing sample collection and testing.

SUMMARY OF THE INVENTION

The present invention is directed to devices for detecting an analyte suspected of being present in a fluid sample. In one embodiment the devices are for detecting analytes of interest in body fluids, such as saliva or oral fluid. The devices have a casing which contains a port for positioning of a sample collection well. The sample collection well has a chamber for collection and storage of a confirmation sample, and contains a plunger which has a raised and a lower position. In some embodiments the sample collection well has an upper and a lower chamber, and the lower chamber is present when the plunger is in the lower position, and also collects fluid sample to be analyzed. The device also has a sample outlet sealed by a frangible material which provides liquid communication between the sample collection well and the test compartment when the sample outlet is open. The device also has an expression plate, which allows the user to express sample into the device from a sample applicator that has an absorbent member for collecting the fluid sample. In some embodiments the lance is attached to the bottom end of the plunger. The sample outlet is opened by moving the plunger to the lower position, which causes the lance to break the frangible material and open the sample outlet, thereby providing liquid communication between the sample collection well and the test compartment. In embodiments where a screw cap is used, the plunger is lowered by screwing on the cap, the bottom of which interacts with the plunger or a piece connected thereto, and forces the plunger into the lower position. Kits containing the devices, and methods of using the devices are also provided.

In a first aspect, the present invention provides a test device for detecting an analyte suspected of being present in a fluid sample. The device has a casing, having a port for a sample collection well. The device further contains a test compartment containing at least one test element. The sample collection well is situated in the port, and has an expression plate, and a plunger having a raised position and a lower position. The device also has a chamber for storage of a confirmation sample. A lance is also contained within the device, and in one embodiment is carried by the plunger. The device also has a sample outlet sealed by a frangible material that provides liquid communication between the sample collection well and the test compartment when the sample outlet is open. The device also has a mp for the sample collection well, where a portion of the cap interacts with the plunger to move the plunger from the raised position to the lower position when the cap is applied to the sample collection well.

The term "plunger" refers to a part of the device that moves through a portion of the device to bring two parts into contact and perform a function in the operation of the device. In one embodiment the plunger moves within a circular or cylindrical part of the device. In some embodiments the plunger carries a lance and serves to deliver the lance to a frangible material that is pierced by the lance. A "lance" is an object that pierces a frangible seal. The lance will typically be sharp or otherwise have the capability to pierce the frangible seal. The "port" is a portion of the device where the casing interfaces with the sample collection well. The port can be an opening into which the sample collection well fits reversibly, or the sample collection well and casing can be produced as a single unit. The port also provides access between the sample collection well and the test compartment.

An "expression plate" refers to a surface where a sample applicator filled with fluid sample can be squeezed or crushed against to express sample from the applicator. The expression plate can have openings or holes to allow the passage of fluid sample from the applicator to the sample collection well. The expression plate can be located within the sample collection well, but can also be placed in another location where expressed sample will flow to the collection well. In one embodiment the expression plate is located in the sample collection well and divides the upper and lower chambers, and has one or more holes or openings through which fluid sample can flow from the upper chamber to the lower chamber. When the sample collector is pressed against the expression plate, sample flows through the opening in the expression plate, into the lower chamber.

The "test element" can be any element that performs a test. In one embodiment, the test element is a test strip. The test strip may contain a member of a specific binding pair on the test strip for conducting an immunoassay. The test strip may be a chemical test strip that provides a detectable color change or other detectable signal when the assay is complete. A variety of samples can be used with the present invention including, but not limited to, a bodily fluid or a sample derived from a biological tissue or a bodily fluid. For example, the sample may be saliva, blood, serum, plasma, urine, feces, spinal fluid, vaginal swabs, mucus, and tissue. In one embodiment, the expression plate divides the upper chamber from the lower chamber, and has an aperture for flow of liquid sample from the upper chamber to the lower chamber.

The "sample outlet" provides liquid communication from the sample collection well to the test compartment. The sample outlet in the device is sealed by a frangible material, and liquid communication does not occur between the sample collection well and test compartment until the frangible seal is pierced or broken by the lance, which is lowered into the frangible material by the plunger to begin the assay.

In one embodiment the sample collection well also has a lower chamber present when the plunger is in the raised position, and an upper chamber where the confirmation sample is stored. In one embodiment the sample collection well contains the plunger, upper and lower chambers, the expression plate, and the sample outlet, however, in other embodiments these components can be located outside the sample collection well. In one embodiment, expression plate divides the upper chamber from the lower chamber, and has an aperture for flow of liquid sample from the upper chamber to the lower chamber. The lance can be carried on the plunger (e.g., on the bottom surface of the plunger), and can be downwardly-projecting and perpendicularly aligned with the sample outlet for breaking the frangible material. The sample collection well and cap can have complementary engaging screw threads. In one embodiment the cap carries a downward projection that interacts with the plunger when the cap is applied to the sample collection well. The expression plate can have an opening through which the projection passes to interact with (and push) the plunger. By "complementary engaging screw threads" is meant that the cap and sample collection well each have screw threads which are complementary and the cap can be screwed onto the sample collection well to obtain a fit by rotation of the cap on the sample collection well and engagement of the screw threads, and where liquid sample does not leak from around the cap.

In certain embodiments of the present invention, the lower chamber is absent when the plunger is in the lower position. This can be due to the lower chamber existing under the plunger, and disappearing when the plunger is lowered and the lance pierces the frangible material. The frangible material can be any material that is pierceable by a lance. Examples of frangible materials include (but are not limited to) paper, wax-coated paper, plastic-coated paper, plastic film, a thin plastic sheet, adhesive tape, foil, waxed foil and plastic-coated foil.

In some embodiments, the test element is a test strip. The test strip may have specific binding molecules immobilized on the test strip, but can also have a chemical test. The fluid sample can be any fluid such as (for example) oral fluid, saliva, blood, serum, plasma, urine, feces, spinal fluid, vaginal swabs, mucus, and tissue. "Saliva" refers to the excretions of the salivary glands. "Oral fluid" is any fluid present in the buccal cavity and saliva is a major component of oral fluid. Any analyte can be detected using the present invention for which a test element exists. For example, the analyte can be a drug (such as a drug of abuse), a hormone, a protein, a peptide, a nucleic acid molecule, an etiological agent and a specific binding pair member. In a further embodiment, the upper and lower chambers are present in the sample collection well when the plunger is in the raised position, and the lower chamber is not present when the plunger is in the lower position. In another embodiment the sample collection well is sealed when the lance punctures the frangible material. The sample collection well can be sealed by seals present on the lower portion of the plunger and/or seals located at or around the reservoir. Thus, when the plunger is lowered the sealing bodies provide a seal to the sample collection well.

In another aspect, the present invention provides a kit having a device described herein, and a sample applicator. In one embodiment of the present invention, the sample applicator has an absorbent member and a handle. The absorbent member may be a sponge, a foam, or any material that absorbs liquid. The absorbent member can be soaked in or pre-treated with a solution that stimulates salivation in a test subject. The kit can also contain instructions for use of the device. In one embodiment the instructions are for use of the device for the detection of an analyte in a fluid sample.

In another aspect the present invention provides methods of detecting the presence of an analyte in a fluid sample. The methods involve applying the fluid sample to a device as described herein, applying the cap to the sample collection well, engaging the plunger and lowering the plunger so that the lance punctures the frangible material and releases the fluid sample into the test compartment, and determining the presence of the analyte in the fluid sample. In certain embodiments, applying the sample includes contacting a sample applicator with the fluid sample, inserting the sample applicator into the sample well, and pressing the sample applicator against the expression plate to express the fluid sample into the sample collection well. The expressed fluid sample flows into the lower chamber of the sample collection well and a portion of the fluid flows from the upper chamber around at least one edge of the plunger and into the lower chamber.

In another embodiment of the present method, after fluid sample is applied to the sample collection well, the cap is applied to the sample collection well and the plunger is lowered to puncture the frangible material as the cap is applied, thereby providing fluid communication between the sample collection well and the test compartment. In certain embodiments, the fluid sample flows from the lower chamber to the test compartment when the plunger punctures the frangible material. The sample collection well and cap can further comprise complementary engaging screw threads. When the cap is screwed onto the sample collection well, a portion of the cap interacts to provide a force onto the plunger and thereby lower the plunger and puncture the frangible material. In one embodiment, the lower chamber is not present when the plunger is in the lower position. The force applied to the plunger may be a direct force from the bottom of the cap to the back of the plunger.

The summary of the invention described above is not limiting and other features and advantages of the invention will be apparent from the following detailed description, as well as from the claims.

DETAILED DESCRIPTION

In the following detailed description, reference is made to the accompanying drawings that form a part hereof, and in which is shown by way of illustration specific embodiments in which the invention may be practiced. It is understood that other embodiments may be utilized and structural changes may be made without departing from the scope of the present invention.

The devices and methods of the present invention enable the easy detection of analytes in fluid samples. The devices also allow a quantity of sample to be easily stored for confirmatory testing later in a reservoir within the device, using a different principle of testing if desired. The confirmation sample is therefore safely stored from contamination. The device also allows the user to control the time of beginning the assay, because the user can apply sample to the sample collection well and fill the sample collection well, but the assay will not begin until the user applies the cap to the sample collection well and lowers the plunger, thereby puncturing the frangible material and releasing the fluid sample into the test compartment. FIGS. 1-6 show only certain embodiments of the present invention for purposes of illustrating the invention, and are not limiting. With reference to the present disclosure the person of ordinary skill will realize other embodiments.

Sample Analysis and Storage Device

The present invention provides a test device for detecting an analyte in a fluid sample, and for storing an aliquot of the sample for confirmation testing. FIGS. 1-6 show one embodiment of the present device 100, which comprises a casing 110, having an injection molded top 210 and base 215. The casing has a test compartment 360 in which are situated test elements for conducting the assay of the invention. There is also a port 120 in which is situated a sample collection well 130. In one embodiment the sample collection has a plunger 240, an upper chamber 320 for storage of a confirmation sample, an expression plate 230 for expressing sample from a sample applicator by wringing or squeezing against the expression plate, a sample outlet 350 sealed by a frangible material 270 and which provides liquid communication between the sample collection well and the test compartment when the sample outlet is open. In other embodiments these components may not be present in the sample collection well. In the embodiment illustrated in FIGS. 4 though 6, the expression plate divides the upper chamber from the lower chamber, and has an aperture 520 for flow of liquid sample from the upper chamber to the lower chamber. Additionally, the plunger has both raised and lowered positions. When the plunger is in the raised position a lower chamber 330 is present in the sample collection well (see FIGS. 3 and 4). When the plunger is in the lowered position, the lower chamber is no longer present (see FIGS. 5 and 6). In other words, the lower chamber disappears when the plunger moves into the lowered position as the space then becomes occupied by the plunger.

Embodiments of the device are possible where no upper and lower chambers are present, but a single chamber performs the functions. The expression plate can also be located at a point removed from the sample collection well, and the fluid sample transferred to the test compartment. Also, the lance can be carried on the plunger, which can be present in the sample collection well (as shown in the Figures), but the lance can also be present as a separate component, either within or outside of the sample collection well.

The plunger may be made of a variety of materials, such as injection-molded or press-molded plastic. The plunger has a face, which is the portion opposite the cap and closest to the sample outlet, and a back which is the portion of the plunger body closest to the cap. The plunger can carry the lance on its face side. The plunger can also have arms which extend towards the cap, so that the bottom of the cap interfaces with the plunger arms to apply force on the plunger and drive it and the lance into the frangible material. The lance is sufficiently sharp and hard to break the fungible material that has been chosen to cover the sample outlet. The lance can be manufactured as an integral part of the injection-molded plastic plunger, or incorporated into the plastic plunger.

Figure 1:
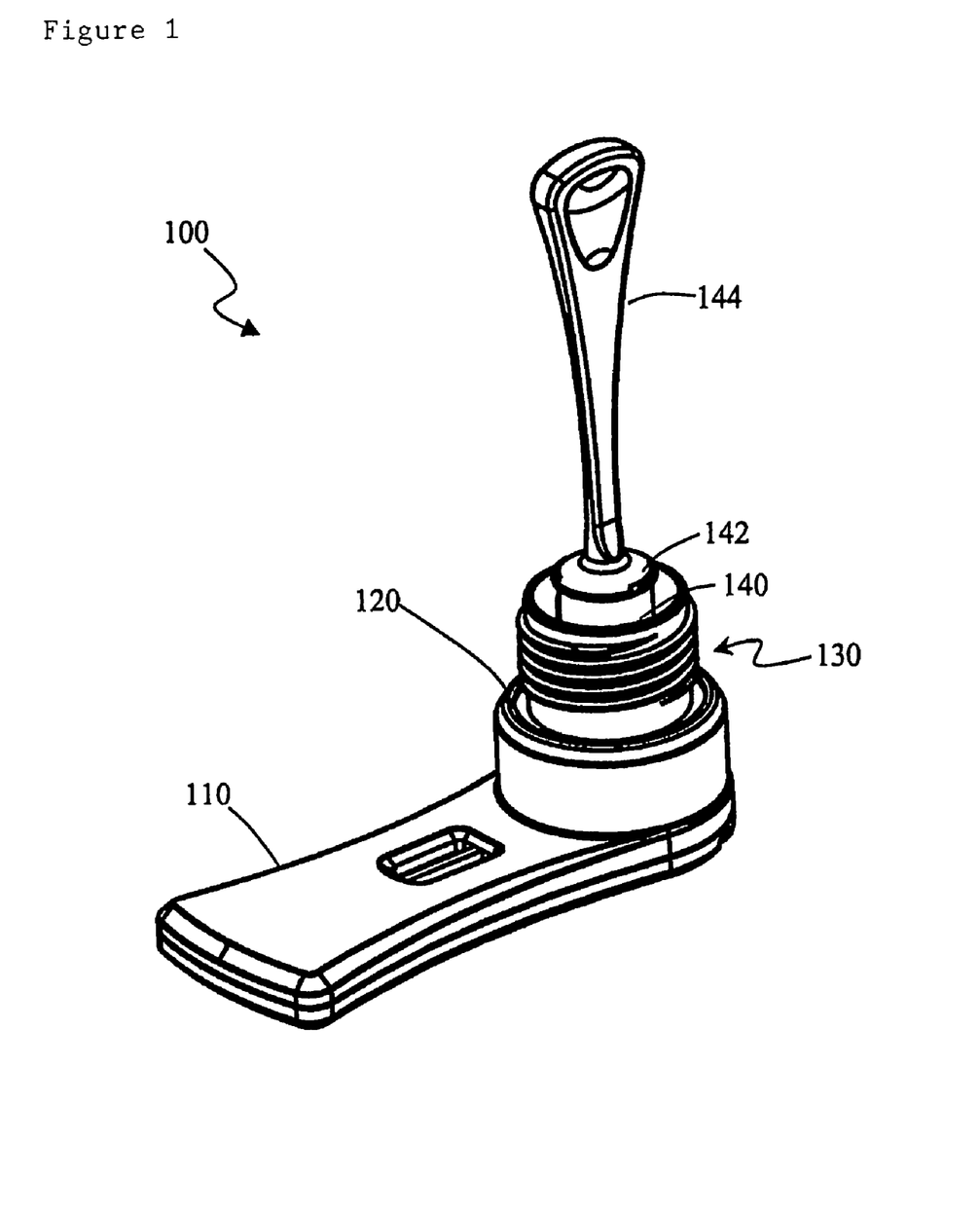
FIG. 1 provides a perspective view of one embodiment of the present invention.
Figure 2:
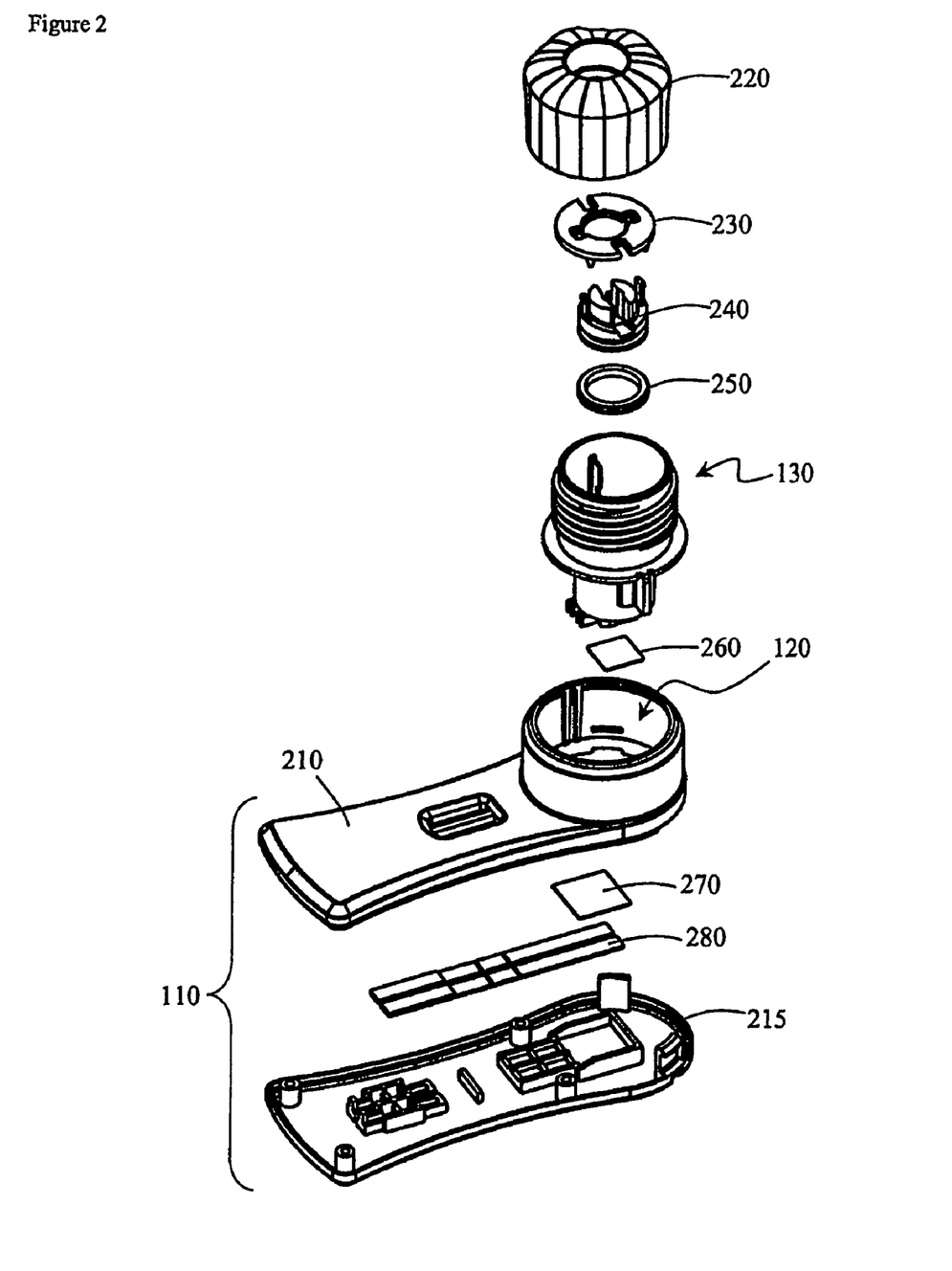
FIG. 2 provides an exploded view of the device shown in FIG. 1.
Figure 5:
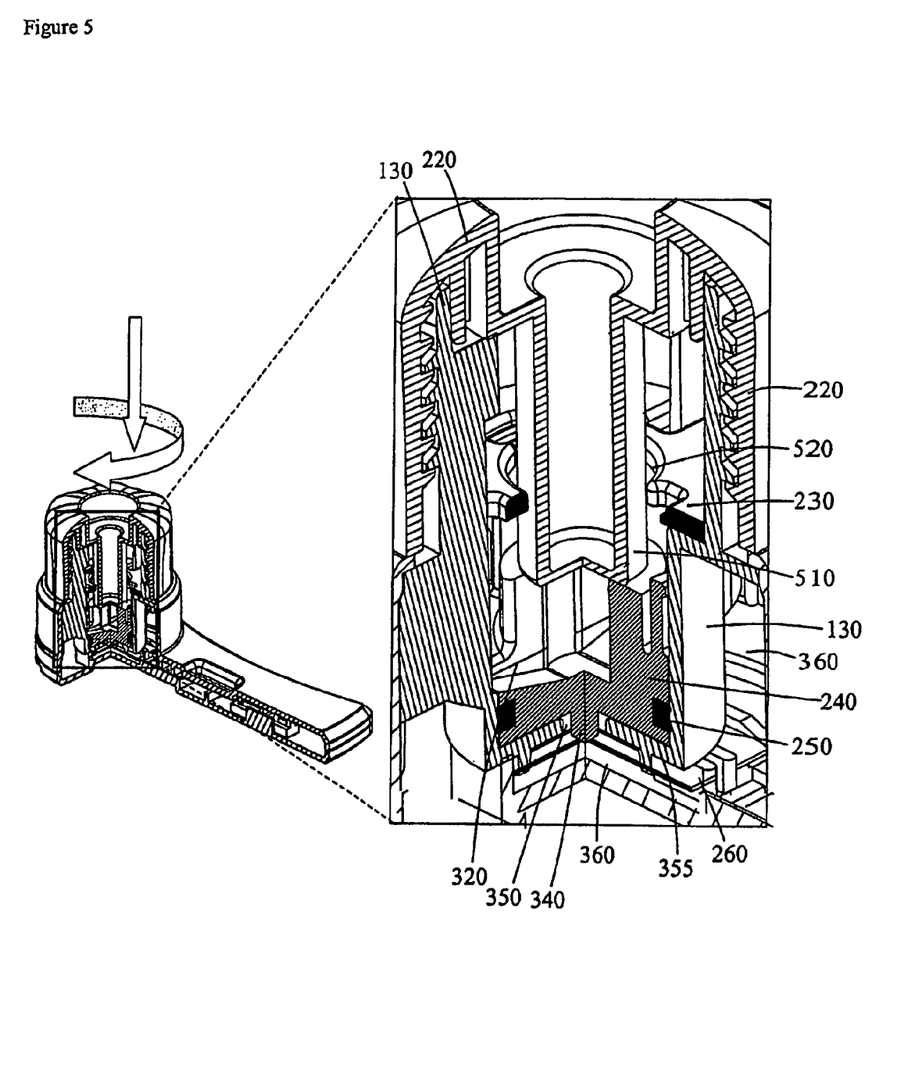
FIG. 5 provides a cut-away view and a magnified view of the device shown in FIG. 1, after use. Note the lance is shown having pierced the frangible material.
Figure 6:
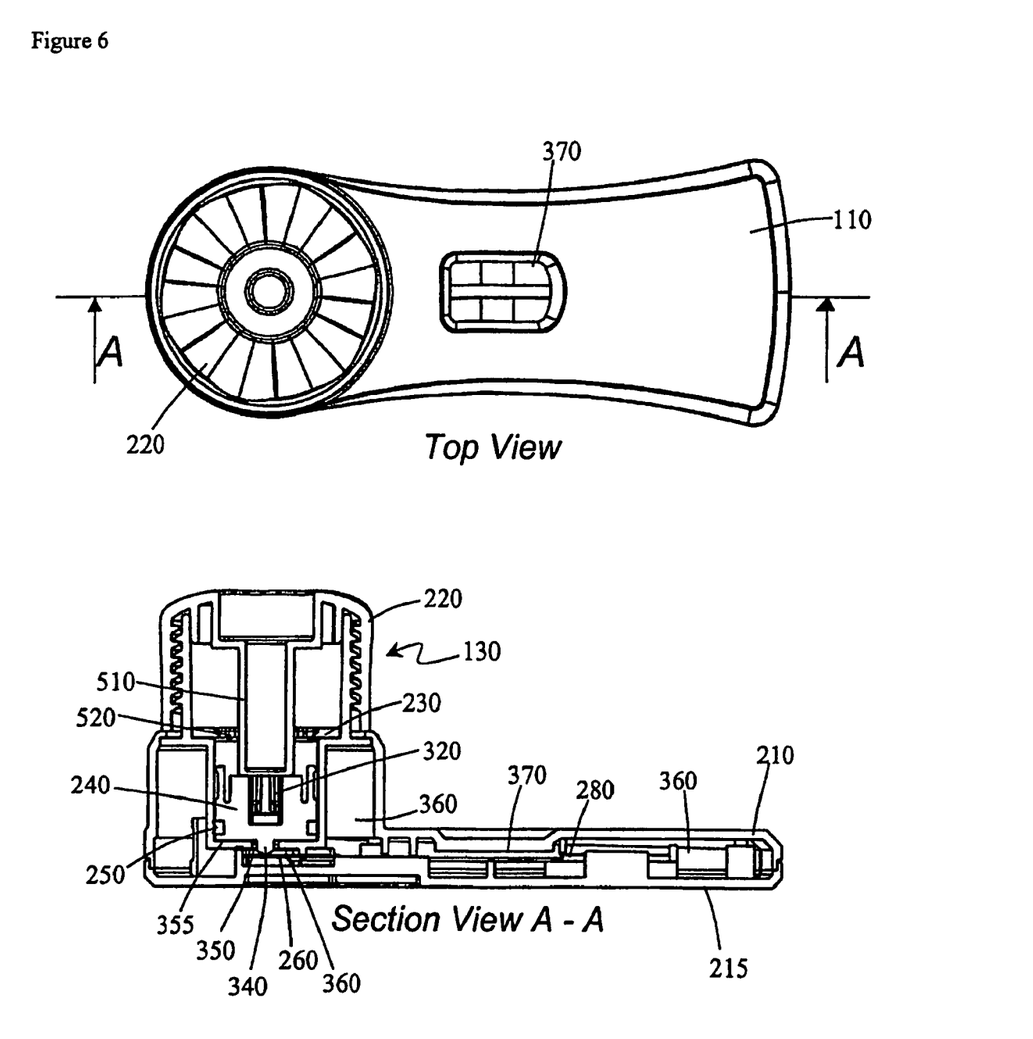
FIG. 6 provides a top view and a section view of the device shown in FIG. 1, after use.

In one embodiment, the device has a cap 220 for the sample collection well (see FIGS. 2, 5 and 6). In one embodiment the sample collection well and cap have complementary engaging screw threads. The cap can have a projection 510 (see FIGS. 5 and 6) that interacts with the plunger, such as a downward projection from the bottom of the cap. The projection can be an extended projection from the center bottom of the cap, but in other embodiments it can be arms extending from the center or sides of the cap, or other projections that extend from the cap and interact directly or indirectly with the plunger. The expression plate has an opening 520 through which the projection passes to interact with the plunger. When the cap is screwed onto the sample collection well, the downward projection of the cap is placed into contact with the plunger and moves it from the raised position to the lowered position. This causes the lower chamber to disappear.

In certain embodiments, the plunger carries a lance 340 on its bottom surface. The lance on the bottom of the plunger can be downwardly-projecting towards the sample outlet, and is aligned with the outlet for breaking the frangible material. In one embodiment the plunger is perpendicularly aligned with the plane of the outlet. As the plunger is moved to its lower position, the lance moves into and punctures the frangible material, and sample in the sample collection well (e.g., from the lower chamber) flows into the test compartment. The frangible material may be made of any convenient material, such as paper, wax-coated paper, plastic-coated paper, plastic film, a thin plastic sheet, adhesive tape, foil, waxed foil and plastic-coated foil. The frangible material may be attached with adhesive.

In one embodiment the lance can also have affixed to its lower edge a seal, so that when the plunger is in the lower position a seal is effected between the sample collection well and the test compartment. The seal can be made of rubber, plastic, or any material that can form a seal over the outlet when the plunger is in the lower position.

Figure 3:
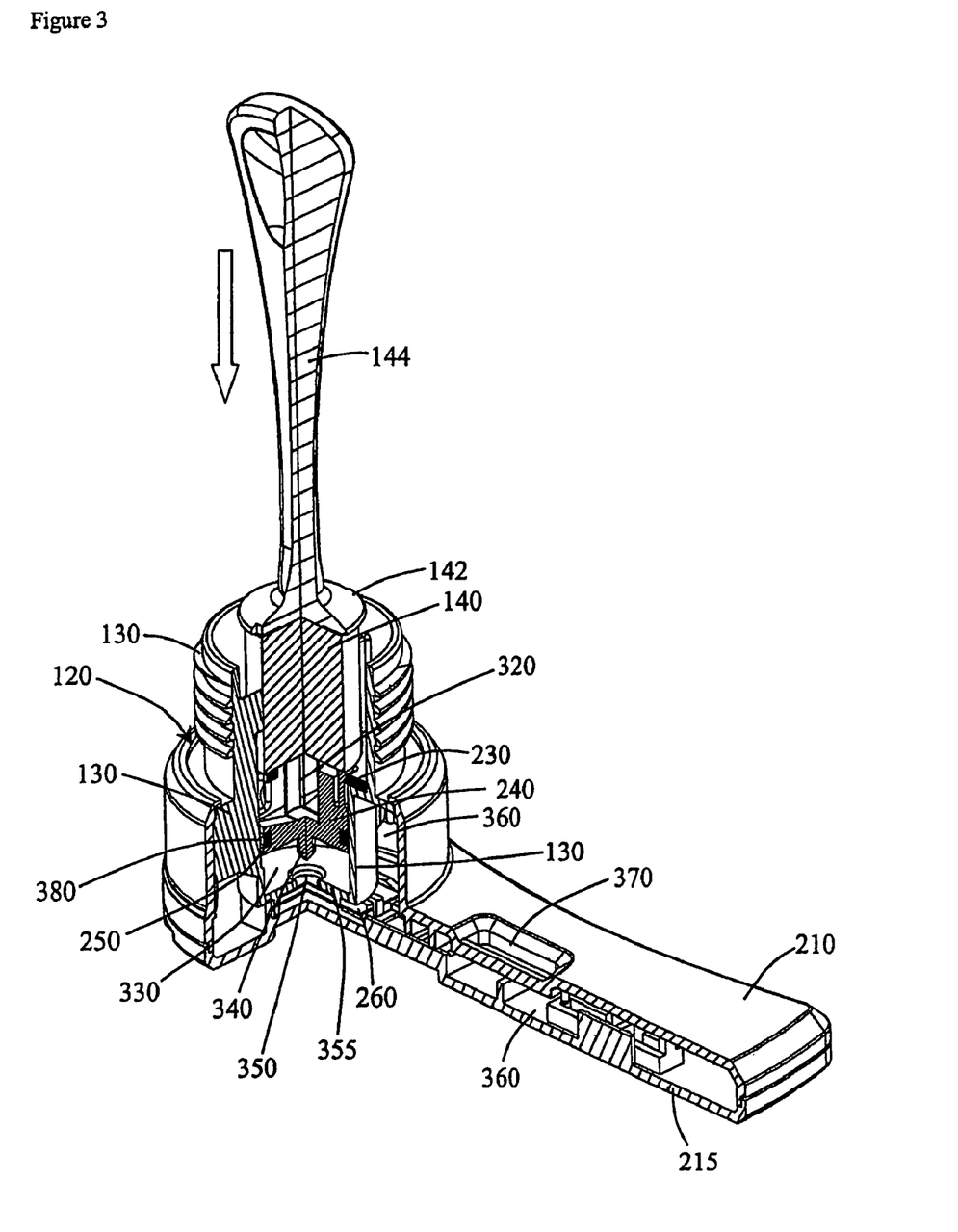
FIG. 3 provides a cut-away view of the device shown in FIG. 1.
Figure 4:
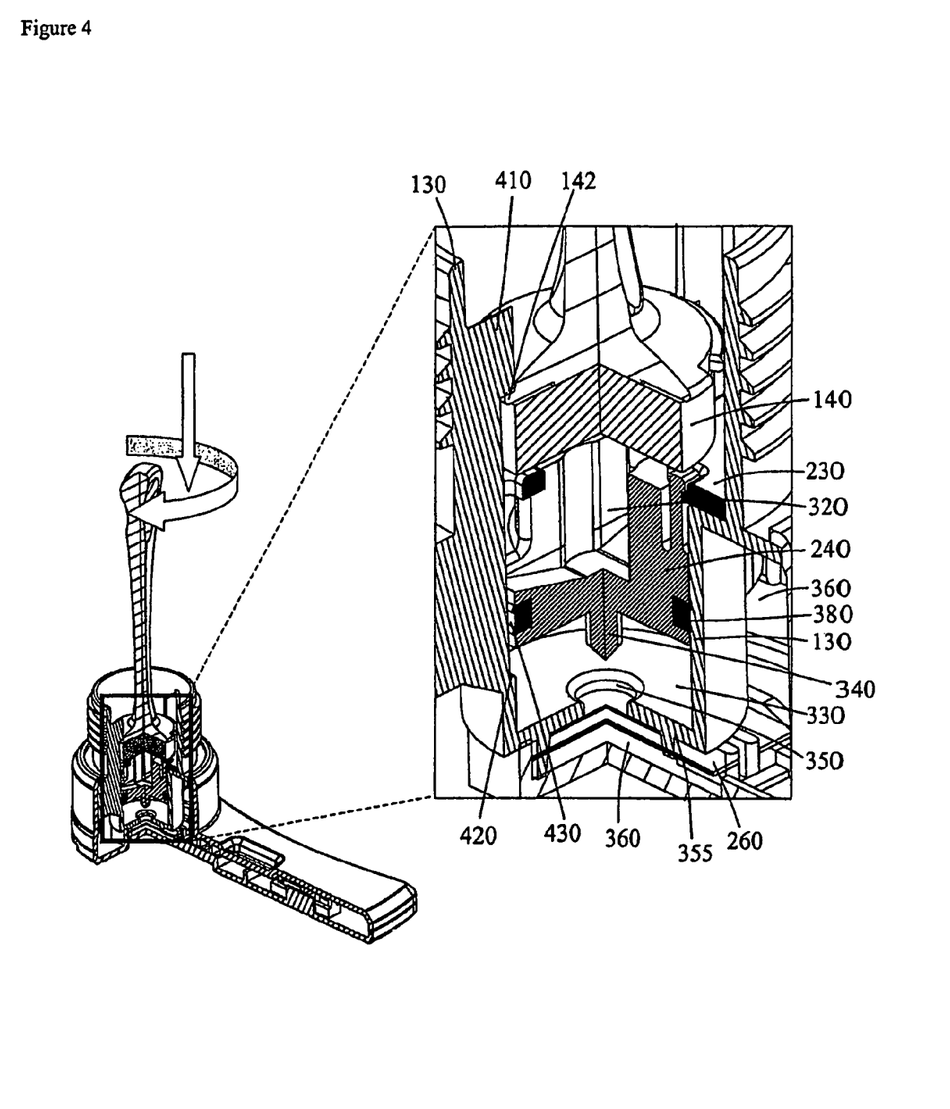
FIG. 4 provides a cut-away view and a magnified view of the device shown in FIG. 1, during use.

As shown in FIGS. 2, 3, 4 and 5, an O-ring 380 is provided around the rim of the plunger. However, any sealing mechanism can also be used. FIG. 4 illustrates a conical shoulder 420 on the wall of the of the sample collection well. In one embodiment, the diameter of the collection well above the shoulder is slightly wider than the diameter of the lower chamber. The plunger is sized to fit snugly into the diameter of the lower chamber and against the bottom of the lower chamber, such that the O-ring and plunger create a seal between the sample collection well and the test compartment. Thus, the sample collection well becomes a reservoir for the sample remaining in the collection well, and which can be preserved in the device and used for confirmation testing. When the plunger is in the raised position, the plunger fits loosely within the diameter of the sample collection well, leaving a small space 430 between the edge of the plunger and the wall of the sample application well, through which a portion of fluid sample flows into the lower chamber. Sample can also flow through openings which exist in some embodiments in the plunger and/or expression plate. The plunger can also have a seal on its face so that when the plunger pierces the frangible material, the plunger continues forward until it mates with the bottom of the sample collection well, forming a seal between the sides of the plunger and the walls of the sample collection well lower chamber, as well as a seal being formed around the sample outlet. Thus, the plunger can carry an O-ring or other type of seal on its face for this purpose. It can also be arranged so that a seal exists on the bottom of the lower chamber of the sample collection well, and that this component forms a seal to close the sample outlet when the plunger in the lower position.

In another embodiment of the present device, the test compartment contains at least one test element 280, for example, a test strip. A variety of analyte test strips can be incorporated into the present invention which is discussed in greater detail below. Sample comes into contact with the test strips when the plunger has been pushed into the lowered position and the frangible seal is broken. When the frangible seal breaks, sample that is present in the lower chamber flows through the sample outlet and contacts the wicking paper 260. The wicking paper moves the sample by capillary action to the sample loading end of the test strips (see below) and the tests are initiated. While the illustrated embodiments use wicking paper, it is also possible to not use wicking paper and allow the sample to flow directly to the test element. The test results can be read through a window 370 provided in the top of the casing. Indicia may be provided next to the window, to indicate to the user where to expect test result lines and control lines.

Sample Applicator

A sample applicator may be supplied with the device of the present invention. In one embodiment the sample applicator has an absorbent member 140 and a handle 144. The absorbent member can be made of medical grade sponge or foam material commonly used in the art. But many other materials are available for use as an absorbent member, such as cotton or paper, or any material having suitable absorbent capacity. The handle is generally rigid, to facilitate manipulation of the absorbent member. The handle may be made of any material commonly employed in the art, such as plastic, wood, metal or cardboard. In one embodiment the handle has a rim 142 (FIG. 1) to which the absorbent member is attached. In some embodiments the absorbent member is soaked in or pre-treated with a material that stimulates salivation in the test subject.

In some embodiments of the present invention, the upper chamber of the sample application well may have ribs. The sample applicator can be adapted so that its rim locks under the ribs when the applicator has been sufficiently pressed against the expression plate and then twisted to fit under the ribs. This may ensure that the absorbent member of the applicator has been sufficiently squeezed for a sufficient amount of time to express as much sample contained therein as possible.

Test Strips

A variety of test elements can be incorporated into the present invention. One type of test element is a test strip. Analyte test strips are test elements provided in a variety of formats, such as immunoassay or chemical test format, for detecting analytes of interest in a sample, such as a drug of abuse or a metabolite suggestive of health status. Test strips can also be provided in either noncompetitive or competitive assay formats. In some formats, the test strips have a bibulous material having a sample application zone, a reagent zone and a test result zone. The sample is applied to the sample application zone and flows into the reagent zone by capillary action. In the reagent zone, the sample dissolves and mixes with reagents necessary for detection of the analyte (if it is present in the sample). The sample, now carrying the reagents, continues to flow to the test results zone. Additional reagents are immobilized in the test results zone, such as a specific binding molecule for the analyte. These reagents react with and bind the analyte (if present) or one of the first reagents from the reagent zone. Labels for forming the detectable signal can be present in the reagent zone, or a separate label zone.

In noncompetitive formats, a signal is produced if the sample contains the analyte, and no signal is produced if the analyte is not present. In competitive formats, a signal can be produced if no analyte is present, and no signal if analyte is present.

When the test element is a test strip, it may be made of bibulous or non-bibulous material. A test strip can include more than one material, which are then in fluid communication. One material of a test strip may be overlaid on another material of the test strip, such as for example, filter paper overlaid on nitrocellulose. Alternatively or in addition, a test strip may include a region comprising one or more materials followed by a region comprising one or more different materials. In this case, the regions are in fluid communication and may or may not partially overlap one another. The material or materials of the test strip can be bound to a support or solid surface such as a supporting sheet of plastic, to increase its handling strength.

In embodiments where the analyte is detected by a signal producing system, such as by one or more enzymes that specifically react with the analyte, one or more components of the signal producing system can be bound to the analyte detection zone of the test strip material in the same manner as specific binding members are bound to the test strip material, as described above. Alternatively or in addition, components of the signal producing system that are included in the sample application zone, the reagent zone, or the analyte detection zone of the test strip, or that are included throughout the test strip, may be impregnated into one or more materials of the test strip. This can be achieved either by surface application of solutions of such components or by immersion of the one or more test strip materials into solutions of such components. Following one or more applications or one or more immersions, the test strip material is dried. Alternatively or in addition, components of the signal producing system that are included in the sample application zone, the reagent zone, or the analyte detection zone of the test strip, or that are included throughout the test strip, may be applied to the surface of one or more test strip materials of the test strip as was described for labeled reagents.

The zones can be arranged as follows: sample application zone, one or more reagent zones, one or more test results determination zones, one or more control zones, one or more adulteration zones, and fluid absorbing zone. If the test results determination zone includes a control zone, preferably it follows the analyte detection zone of the test result determination zone. All of these zones, or combinations thereof, can be provided in a single strip of a single material. Alternatively, the zones are made of different materials and are linked together in fluid communication. For example, the different zones can be in direct or indirect fluid communication. In this instance, the different zones can be jointed end-to-end to be in fluid communication, overlapped to be in fluid communication, or be communicated by another member, such a joining material, which is preferably bibulous such as filter paper, fiberglass or nitrocellulose. In using a joining material, a joining material may communicate fluid from end-to-end joined zones or materials including such zones, end-to-end joined zones or materials including such zones that are not in fluid communication, or join zones or materials that include such zones that are overlapped (such as but not limited to from top to bottom) but not in fluid communication.

When and if a test strip includes an adulteration control zone, the adulteration control zone can be placed before or after the results determination zone. When a control zone is present in the results determination zone on such a test strip, then the adulteration control zone is preferably before the control zone, but that need not be the case. In the embodiment of the present invention where a test strip is a control test strip for the determination of an adulteration analyte and/or a control, then the adulteration control zone can be placed before or after the control zone, but is preferably before the control zone. The reagents used in the adulteration assay determine whether there has been an attempt to defeat the purpose of the assay by the test subject, such as by adding material to the sample to change the results of the assay.

Samples that can be tested with the device of the present invention include liquids of biological origin (e.g., casing fluids and clinical samples). Liquid samples may be derived from solid or semi-solid samples, including feces, biological tissue, and food samples. Such solid or semi-solid samples can be converted into a liquid sample by any suitable method, for example by mixing, chopping, macerating, incubating, dissolving or enzymatically digesting solid samples in a suitable liquid (e.g., water, phosphate-buffered saline, or other buffers). "Biological samples" include samples derived from living animals, plants, and food, including for example urine, saliva, blood and blood components, cerebrospinal fluid, vaginal swabs, semen, feces, sweat, exudates, tissue, organs, tumors, tissue and organ culture, cell cultures and conditioned media therefrom, whether from humans or animals. A preferred biological sample is urine. Food samples include samples from processed food components or final products, meat, cheese, wine, milk and drinking water. Plant samples include those derived from any plant, plant tissue, plant cell cultures and conditioned media therefrom. "Environmental samples" are those derived from the environment (e.g., a water sample from a lake or other casing of water, effluent samples, soil samples, ground water, ocean water, and runoff water. Sewage and related wastes can also be included as environmental samples.

Any analyte can be tested for utilizing the present invention and a suitable test element. In particular, the present invention can be utilized for the detection of a drug of abuse in oral fluid. A "drug of abuse" (DOA) is a drug that is taken for non-medicinal reasons (usually for mind-altering effects). The abuse of such drugs can lead to physical and mental damage and (with some substances) dependence, addiction and/or death. Examples of DOAs include cocaine; amphetamines (e.g., black beauties, white bennies, dextroamphetamines, dexies, beans); methamphetamines (crank, meth, crystal, speed); barbiturates (Valium®, Roche Pharmaceuticals, Nutley, N.J.); sedatives (i.e. sleep-aids); lysergic acid diethylamide (LSD); depressants (downers, goofballs, barbs, blue devils, yellow jackets, ludes); tricyclic antidepressants (TCA, e.g., imipramine, amitriptyline and doxepin); phencyclidine (PCP); tetrahydrocannabinol (THC, pot, dope, hash, weed, etc.); and opiates (e.g., morphine, opium, codeine, heroin, oxycodone).

Additional analytes that can be tested using the present invention include but are not limited to creatinine, bilirubin, nitrite, protein (nonspecific), hormones (e.g. human chorionic gonadotropin, luteinizing hormone, follicle stimulating hormone, etc.), blood, leukocytes, sugar, heavy metals or toxins, bacterial components (e.g. proteins or sugars specific to a particular type of bacteria, such as *E. coli*0157:H7, *S. aureus, Salmonella, C. perfringens, Carnpylobacter, L. monocytogenes, V. parahaemolyticus,* or *B. cereus*) and physical characteristics of the urine sample, such as pH and specific gravity. Any other clinical urine chemistry analyte that can be adapted to a lateral flow test format may also be incorporated into the present device.

Methods of Use

The following discussion relates to those embodiments illustrated in the examples. Of course other embodiments are possible without departing from the scope of this invention. In the methods of the invention, the step of applying the sample to the device can include contacting a sample applicator with the fluid sample, for example, by inserting it into the mouth of a test subject or by immersing it in a container of fluid sample. The filled or soaked applicator 144 can be inserted into the sample collection well 130, and the applicator pressed or squeezed against the expression plate 230 to express the fluid sample into the sample collection well (see FIG. 4). The expressed fluid sample flows into the lower chamber of the sample collection well through openings in the expression plate, or through spaces 430 present at the sides of the plunger 240 (FIG. 3). Thus, a portion of the fluid flows from the upper chamber around an edge of the plunger and into the lower chamber 330.

After sample is completely expressed, the cap 220 can be applied to the sample collection well (see FIGS. 2 and 5). When the cap and sample collection cup contain complementary engaging screw threads, the cap is screwed onto the sample collection well. The cap can contain a part or projection that interacts with the plunger. For example, the center bottom of the cap can contain a projection that extends downward through the center of the expression plate and is therefore placed on the back of the plunger to exert the force. The interaction can be simply the physical contact and transfer of force to the plunger applied by the downward motion of the cap. This force causes the plunger to be lowered within the sample collection cup as the cap is screwed on, and for the lance carried on the plunger to be lowered into the frangible material, and thereby puncture it. Thus, fluid communication is provided between the sample collection well and the test compartment. Fluid then flows from the sample collection well to the test compartment, and the assaying begins. In other embodiments, the cap can be snapped onto the top of the sample collection well, or otherwise applied so that sample does not leak out, and force is applied to the plunger. FIG. 5 shows the plunger in the lowered position and that the lance has punctured the frangible material, thereby opening the sample outlet. The Figures also show an absorbent wicking paper 260 placed below the sample outlet, which can be used to enhance flow of the fluid sample from the sample collection well to the test elements. The wicking paper can be made of any convenient bibulous material capable of capillary flow. Examples include glass fiber paper and polyester mesh treated to become hydrophilic and filter paper. After the control indicia are provided, the result of the assay is conveniently determined by viewing the test element through the window 370.

Test Kits

Test kits of the invention can be packaged in a variety of formats, depending upon the Customer's needs. For example, a facility that conducts large numbers of pre-employment drug screenings may prefer boxes of 1 set of instructions plus 20 vacuum packed set of devices and applicators. On the other hand, other users may prefer boxed kits that contain only one device, one sample collector, and one set of instructions. Any suitable packaging materials can be used. Test kits may be packaged in a box, or may be wrapped in protective material such as cellophane. Test kits may also be provided with a test device (and applicator) provided in the same or separate sealed pouches, which may or may not then be provided in a box or other packaging.

EXAMPLE 1

Pre-Employment Drug Screening

The devices of the invention can be utilized in a variety of contexts. This example illustrates a use of the device for pre-employment drug screening. The person to be tested provides a sample of saliva by placing the sample applicator into his or her mouth, and allowing it to remain in the mouth for about 5 minutes. In embodiments for pre-employment drug screening the device contains lest strips for several common drugs of abuse, in this embodiment cocaine, methamphetamine, phencyclidine, THC, morphine, and amphetamines. The device utilizes test strips in a competitive immunoassay format where labeled specific binding molecules (antibodies labeled with gold sol in this embodiment) for each drug being tested are present on the label zone of the test strip. The test lines contain the antigen being tested for. If analyte is present in the sample it is bound by labeled specific binding molecules in the label zone, thereby preventing the labeled antibody from binding to the test line. Thus, no signal occurs on the test line when analyte is present. Conversely, when no antigen is present in the sample, the labeled antibodies bind to the test line providing the signal on the test line.

After receiving the filled or soaked sample applicator, the testing technician inserts it into the sample collection well of the device. The technician presses the applicator down into the well and then twists it, to lock the rim of the applicator under a pair a flanges 410 (provided in this embodiment). Saliva is thereby expressed from the absorbent foam of the sample applicator and flows through the orifice in the expression plate and into the chamber below the expression plate. Since the plunger is in the first position, some of the sample flows around the edges of the plunger into the lower chamber of the sample collection well. When all sample is expressed from the foam, the applicator is removed and the cap is screwed onto the sample collection well. As the cap is screwed onto the sample collection well, the downward projection of the cap pushes the plunger from the raised position to the lowered position, thereby driving the lance into the frangible seal, breaking the seal, and opening the sample outlet. Sample then flows into the test compartment, where it comes into contact with the test strips. At the same time, the portion of the sample remaining in the upper chamber, above the plunger is isolated from the rest of the apparatus, because the plunger becomes a seal between the upper chamber and the test compartment and thereby creating a reservoir to hold the remaining sample. After a few minutes, the control indicia are provided on the test elements, indicating that the assay is complete. A signal is provided at each of the test lines, indicating that no drugs of abuse are present in the saliva sample (competitive assay format). If a positive result is determined, the device may be sent to a confirmatory laboratory so that the sample contained in the reservoir can be tested to confirm the result.

With reference to the present disclosure the person of ordinary skill in the art will realize that any analyte for which a test element is available or later developed can be used in the present invention. Thus, any other drugs of abuse of interest can be tested for, and several example are listed herein. Similarly, any analyte from any sample type can be tested for.

The invention illustratively described herein may be practiced in the absence of any element or elements, limitation or limitations that are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by various embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

We claim:

1. A test device for detecting an analyte suspected of being present in a fluid sample, comprising:
    a casing, comprising a port for a sample collection well;
    a sample collection well situated in the port, the sample well comprising an expression plate and a plunger, the plunger having a raised position and a lower position, the sample collection well further comprising a lower chamber when the plunger is in the raised position;
    an upper chamber for storage of a confirmation sample;
    a test compartment containing at least one test element;
    a sample outlet sealed by a frangible material and providing liquid communication between the sample collection well and the test compartment when the sample outlet is open;
    a lance for piercing the frangible material; and
    a cap for the sample collection well, wherein a portion of the cap interacts with the plunger to move the plunger from the raised position to the lower position when the cap is applied to the sample collection well.

2. The device of claim 1 wherein the lance is carried on the plunger.

3. The test device of claim 1, wherein the expression plate divides the upper chamber from the lower chamber, and comprises an aperture for flow of liquid sample from the upper chamber to the lower chamber.

4. The device of claim 1 wherein the lance is downwardly-projecting and is perpendicularly aligned with the outlet for breaking the frangible material.

5. The device of claim 1 wherein the sample collection well and cap further comprise complementary engaging screw threads.

6. The device of claim 1 wherein the cap comprises a downward projection that interacts with the plunger when the cap is applied to the sample collection well.

7. The device of claim 6 wherein the expression plate comprises an opening through which the projection passes to interact with the plunger.

8. The device of claim 1 wherein the lower chamber is absent when the plunger is in the lower position.

9. The device of claim 1 wherein the frangible material is selected from the group consisting of paper, wax-coated paper, plastic-coated paper, plastic film, a thin plastic sheet, adhesive tape, foil, waxed foil and plastic-coated foil.

10. The device of claim 1 wherein the test element is a test strip.

11. The device of claim 1 wherein the test strip comprises specific binding molecules immobilized on the test strip.

12. The device of claim 1 the test strip further comprising a chemical test.

13. The device of claim 1 wherein the fluid sample is selected from the group consisting of oral fluid, blood, serum, plasma, urine, feces, spinal fluid, vaginal swabs, mucus, and tissue.

14. The device of claim 13 wherein the fluid sample is saliva.

15. The device of claim 1 wherein the analyte is selected from the group consisting of a drug, a hormone, a protein, a nucleic acid molecule, an etiological agent and a specific binding pair member.

16. The device of claim 15 wherein the analyte is a drug of abuse.

17. The device of claim 2 wherein the upper and lower chambers are present when the plunger is in the raised position, and the lower chamber is not present when the plunger is in the lower position.

18. A kit comprising:
a device comprising
a casing, comprising a port for a sample collection well;
a sample collection well situated in the port, the sample collection well comprising an expression plate and a plunger, the plunger having a raised position and a lower position, the sample collection well further comprising a lower chamber when the plunger is in the raised position;
an upper chamber for storage of a confirmation sample;
a test compartment containing at least one test element;
a sample outlet sealed by a frangible material and providing liquid communication between the sample collection well and the test compartment when the sample outlet is open;
a lance for piercing the frangible material;
a cap for the sample collection well, wherein a portion of the cap interacts with the plunger to move the plunger from the raised position to the lower position when the cap is applied to the sample collection well; and
a sample applicator.

19. The kit of claim 18 wherein the lance is carried on the plunger.

20. The kit of claim 19 wherein the sample applicator further comprises an absorbent member and a handle.

21. The kit of claim 20 wherein the absorbent member comprises a sponge.

22. The kit of claim 20 wherein the absorbent member comprises a foam.

23. The kit of claim 20 wherein the absorbent member comprises a solution that stimulates salivation in a test subject.

* * * * *